United States Patent [19]
Dickhaut et al.

[11] Patent Number: 6,121,322
[45] Date of Patent: Sep. 19, 2000

[54] AZULENE DERIVATIVES

[75] Inventors: Joachim Dickhaut, Heidelberg; Walter-Gunar Friebe; Frank Grams, both of Mannheim; Rainer Haag, Ladenburg; Herbert Leinert, Heppenheim, all of Germany

[73] Assignee: Boehringer Mannheim GmbH, Mannheim, Germany

[21] Appl. No.: 09/198,722

[22] Filed: Nov. 24, 1998

[30] Foreign Application Priority Data

Dec. 13, 1997 [EP] European Pat. Off. .............. 97121997

[51] Int. Cl.[7] ....................... A61K 31/185; C07C 229/28
[52] U.S. Cl. ......................... 514/577; 514/507; 558/169; 560/19; 560/313
[58] Field of Search .................................. 514/509, 577; 558/169; 560/19, 313; 564/101

[56] References Cited

U.S. PATENT DOCUMENTS 4,595,700   6/1986   Donald et al. .

FOREIGN PATENT DOCUMENTS

| 320118 | 6/1989 | European Pat. Off. . |
| 497192 | 8/1992 | European Pat. Off. . |
| 197 48 040 | 5/1998 | Germany . |
| 2318789 | 5/1998 | United Kingdom . |
| WO 9209563 | 6/1992 | WIPO . |
| WO 99/00118 | 1/1999 | WIPO . |
| WO 99/00355 | 1/1999 | WIPO . |

OTHER PUBLICATIONS

R. P. Robinson, et al. Bioorg. Med. Chem. Lett. vol. 6, No. 14, 1996, pp. 1719–1724.
Abstract corresponding to WO 99/00355 (Jan. 7, 1999).
Abstract corresponding to WO 99/00118 (Jan. 7, 1999).
Proc. Natl. Acad. Sci. USA 1996 vol. 93, pp. 5127–5130.
Exp. Opin. Ther. Pat. 1996, vol. 6, pp. 1147–1164.
Pharmacol. Rev. 1993, vol. 45, pp. 87–146.
Bioorg. Med. Chem. Lett. 1996, vol. 6, pp. 2317–2322.
Moss, et al., Nature, 1996, vol. 385, pp. 733–736.
Birkedal–Hansen, H. et al., Crit. Rev. Oral Biol. Med. 1993, vol. 4, pp. 197–250.
Nigel, R.A., Beeley et al., Curr. Opin. Ther. Patents 1994, 4(1), pp. 7–16.
J. Biol. Chem. 1994, vol. 269, pp. 22477–22480.
J. Med. Chem. 1998, vol. 41, pp. 266–270.
Pharmacol. Toxicol, 1996, vol. 78, pp. 44–49.
Lancet, 1994, vol. 344, pp. 1105–1110.
Dullemen et al., Gastroenterology 1995, vol. 109, pp. 129–135.
Science 1996, vol. 271, pp. 360–362.

*Primary Examiner*—Joseph McKane
*Assistant Examiner*—Ebenezer Sackey
*Attorney, Agent, or Firm*—George W. Johnston; Patricia S. Rocha-Tramaloni; Robert A. Silverman

[57] ABSTRACT

The invention provides novel azulene derivatives of general formula I

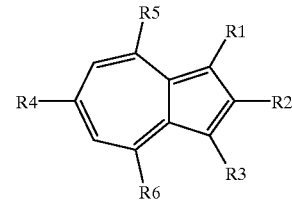

wherein $R_1$ to $R_6$ have the significance given in the description, as well as their tautomers, enantiomers, diastereomers, racemates and physiologically compatible salts or esters and substances which are hydrolyzed or metabolized in vivo to compounds of formula I.

The invention is also concerned with a process and intermediates for the manufacture of the above compounds, pharmaceutical compositions which contain such compounds as well as the use of these compounds in the treatment of inflammatory conditions.

30 Claims, No Drawings

AZULENE DERIVATIVES

BACKGROUND OF THE INVENTION

Metalloproteins play an important role in many physiological and pathophysiological processes. The metalloproteins are accordingly divided into various groups corresponding to their substrate. Many metalloproteins hydrolyze proteins (metalloproteases), while others cleave ester groups (e.g. phosphodiesterases). Examples of metalloproteases are Angiotensin Converting Enzyme (ACE) and the neutral endopeptidases (NEP, EC 3.4.24.11), which participate in the metabolism of a series of blood pressure-regulating peptides (e.g. angiotensin I and ANF (atrial natriuretic factor)). ACE catalyzes the cleavage of angiotensin I to the blood pressure-lowering angiotensin II. NEP is responsible for the degradation of the vasodilating peptide ANF. Endothelin Converting Enzyme (ECE) cleaves the endogenous, inactive big-endothelin to the effective vasoconstrictor endothelin-1, a peptide consisting of 21 amino acids. The inhibition of these enzymes has a great therapeutic significance for the treatment of high blood pressure, cardiac insufficiency, kidney failure and apoplexy. BMP-1 (bone morphogenic factor 1) has been recognized as a metalloprotease which plays a role in the conversion of procollagen into fibrillary collagen. Inhibitors of this enzyme are suitable for the treatment of fibroses and sclerotic processes and can also favourably influence scar formation in the healing of wounds (*Proc. Natl. Acad. Sci. USA* 1996, 93, 5127, *Science* 1996, 271, 360).

While ACE inhibitors are already used therapeutically (e.g. captopril, enalapril, *Exp. Opin. Ther. Pat.* 1996, 6,1147), no clinically useful active substances which are free from undersirable side effects and which are orally available are known for the metalloproteases such as NEP and ECE (literature references: NEP: *Pharmacol. Rev.* 1993, 45, 87; ECE: *Bioorg. Med. Chem. Lett.* 1996, 6, 2317, literature re phosphoramido type inhibitors). Hitherto, no low molecular inhibitors for BMP-1 are known.

The matrix metalloproteases (MMPs) represent one group of metalloproteases. Various groups of metalloproteases are known. One such group is as known as the matrix metalloproteases (MMPs). In normal tissue an equilibrium exists between the synthesis and degradation of the extracellular matrix. The extracellular matrix is synthesized by at least three groups of proteases, namely collagenases, gelatinases and stromelysins. Normally, specific inhibitors of these enzymes, such as e.g. $\alpha_2$-macroglobulin and TIMP (tissue inhibitor of metalloproteases), make sure that an excessive degradation of the extracellular matrix does not take place. A related group of proteases comprises the adamalysins with their most prominent member being TNF-$\alpha$ converting enzyme (TACE) (Moss et al., *Nature* 1996, 385, 733).

At least 11 different, but very homologous matrix metalloproteases have been characterized, inter alia the interstitial fibroblast collagenase (MMP-1, HFC), the neutrophilic collagenase (MMP-8, HNC), two gelatinases, stromelysins (e.g. HSL-1) and matrilysin (Birkedal-Hansen, H., Moore, W. G. I., Bodden, M. K. Windsor, L. J., Birkedahl-Hansen, B., DeCarlo, A., Engler, J. A., *Crit. Rev. Oral Biol. Med.* 1993, 4, 197–250). These proteinases share a series of structural and functional properties, but differ in their substrate specificity. Only HNC and HFC cleave native triple helical collagen of types I, II and III. Fragments of ¾ and ¼ of the original length thereby result. The melting point of the collagen is lowered by this degradation. Subsequently, it can be attacked by other matrix-degrading enzymes.

The uncontrolled excessive degradation of these matrices is typical for many pathological situations which manifest themselves, such as e.g. rheumatoid arthritis, osteoarthritis, multiple sclerosis, tumour metastasing, corneal ulcerations, inflammatory processes and various disorders of the bones and teeth.

The pathogenesis of these illnesses should be positively influenced by the administration of metalloproteinase inhibitors. Some of such compounds are to be found in the literature (a review will be found e.g. in Nigel R. A., Beeley et al., *Curr. Opin. Ther. Patents* 1994, 4(1), 7). These are primarily peptides having a hydroxamic acid, thiol or phosphine residue as the zinc-binding group (inter alia e.g. WO-A-9209563 of Glycomed, EP-A-497192 of Hoffmann-La Roche, WO-A-489577 of Celltech, EP-A-320118 of Beecham, U.S. Pat. No. 4,595,700 of Searle).

Phosphodiesterases (PDEs) are a group of proteins which hydrolyze the regulatory-acting cyclic nucleotides (cAMP or CGMP) in cells to the inactive mononucleotides. The distribution of the PDE isoenzymes differs in individual types of cell. Thus, the isoform is quite prominent in monocytes/macrophages, the cells which synthesize the main amount of proinflammatory Tumour Necrosis Factor $\alpha$ (TNF$\alpha$). A zinc-binding domain in the catalytic centre has been detected for this enzyme and, moreover, its activity is dependent on divalent cations (J. Biol. Chem. 1994, 269, 22477), rolipram inhibits PDE4 and thereby brings about an inhibition of the synthesis of TNF$\alpha$ in vitro and in vivo (J. Med. Chem. 1998, 41, 266). The further development of rolipram has, however, been severely disrupted by massive side effects (Pharmacol. Toxicol. 1996, 78, 44). PDE-inhibitors, which have an improved compatibility based on a selective activity profile, can play a great rôle as inhibitors of TNF$\alpha$ synthesis. Moreover, PDEs can dilate the smooth musculature in the bronchi by increasing cellular cAMPs, which is utilized in the treatment of asthma therapeutically with e.g. theophylline.

Tumor necrosis factor $\alpha$(TNF$\alpha$) is a proinflammatory cytokine which has pathogenetic significance in a large number of illnesses. Clinically it has been shown in a multicentre, randomized double-blind study by Elliot et al. (*Lancet* 1994, 344, 1105–1110) that a neutralizing antibody against TNF$\alpha$ brings about a rapid and pronounced improvement of the disease symptoms in patients with rhumatoid arthritis. In the meanwhile, clinical data has been published by Dullemen et al. in *Gastroenterology* 1995, 109. 129–135 which demonstrates a therapeutic activity of such an antibody in patients with Crohn's disease. Furthermore, it has been shown in animal experiments that rolipram, which likewise blocks the synthesis of TNF$\alpha$, has a very good activity in animal models for multiple sclerosis. Thalidomide, a further TNF$\alpha$-inhibiting substance, has been used clinically for the treatment for chronic graft versus host disorders, in the treatment of nodular leprosy and of patients with lupus erythematodes. Moreover, it has been shown that this substance supresses the proliferation of HIV.

TNF$\alpha$ appears to have direct pathogenic significance in the following disease conditions:

degenerative joint diseases, rheumatoid arthritis, inflammation, allergy, ARDS, asthma, cardiac infarction, chronic cardiac insufficiency, HIV infection, Crohn's disease, ulcerative colitis, psoriasis, dermatitis, actinokeratoses, vasculitides, septic shock, transplant rejection, multiple sclerosis, ulcers, diabetes, chronic graft versus host disorders, leprosy and other infectious diseases, lupus erythematodes, paradontoses and in the case of other illnesses.

The clinical use of monoclonal anti-TNFα antibodies can only by effected parenterally. The medicament is expensive to manufacture and requires a complex distribution logistic (refrigeration network, storage, expiry date etc.). Moreover, in 50% of patients who have received between 2 and 4 injections, the appearance of neutralizing HACAs (human anti-chimeric antibodies) has been established. This means that the trouble-free phases become shorter and shorter. The development of rolipram as an anti-TNFα therapy principle is impaired by its emetic activity. The teratogenic side effects of thalidomide and the weak TNFα blockade can likewise appear to be difficulties in a clinical development of this substance.

SUMMARY OF THE INVENTION

The present invention relates to novel azulene derivatives of general formula I,

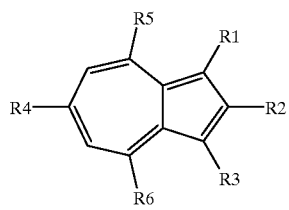

wherein $R_1$ and $R_3$
each independently signify hydrogen, hydroxy, amino, mercapto, an aliphatic group containing 1–15 carbon atoms, which can carry one or more substituents; an alkoxy, alkylamino, dialkylamino, alkylmercapto, alkylsulphinyl, alkylsulphonyl, alkenyl, alkynyl, alkenyloxy, alkenylmercapto, alkynyloxy, alkynylmercapto, alkylcarbonylamino, dialkylcarbonylamino, alkylaminocarbonyl, formyl, alkylcarbonyl, carboxyl, alkoxycarbonyl, alkenyloxycarbonyl, alkynyloxycarbonyl, carboxyalkyl, alkyloxycarbonylalkyl, alkenyloxy; carbonylalkyl, alkynyloxycarbonylalkyl, nitro, cyano, halo, trifluoromethyl or azido group; or phenyl or phenylcarbonyl, which can carry one or more same or different substituents, a mono, bi- or tricyclic carbocyclic group containing 7–15 C atoms or a mono-, bi- or tricyclic heterocyclic ring system, $R_2$
signifies hydrogen, hydroxy, amino, mercapto, an aliphatic group containing 1–15 carbon atoms, which can carry one or more substituents; an alkoxy, alkylamino, dialkylamino, alkylmercapto, alkylsulphinyl, alkylsulphonyl, alkenyl, alkynyl, alkenyloxy, alkenylmercapto, alkynyloxy, alkynylmercapto, alkylcarbonylamino, dialkylcarbonylamino, alkylaminocarbonyl, formyl, alkylcarbonyl, carboxyl, alkoxycarbonyl, alkenyloxycarbonyl; alkynyloxycarbonyl, carboxyalkyl, alkyloxycarbonylalkyl, alkenyloxycarbonylalkyl, alkynyloxycarbonylalkyl, nitro, cyano, halo, trifluoromethyl or azido group; or phenyl or phenylcarbonyl, which can carry one or more same or different substituents, a mono-, bi- or tricyclic carbocyclic group containing 7–15 C atoms or a mono-, bi- or tricyclic heterocyclic ring system, $R_4$
signifies $R_8XON(R_7)COCH_2$—, $R_5$ and $R_6$
each individually signify hydrogen, an aliphatic group containing 1–15 carbon atoms, which can carry one or more substituents; an alkoxy, alkylamino, dialkylamino, alkylmercapto, alkylsulphinyl, alkylsulphonyl, alkenyl, alkynyl, alkenyloxy, alkenylmercapto, alkynyloxy, alkynylmercapto, alkylcarbonylamino, dialkylcarbonylamino, alkylaminocarbonyl, formyl, alkylcarbonyl, carboxyl, alkoxycarbonyl, alkenyloxycarbonyl, alkynyloxycarbonyl, carboxyalkyl, alkyloxycarbonylalkyl, alkenyloxycarbonylalkyl, alkynyloxycarbonylalkyl, nitro, cyano, halo, trifluoromethyl or azido group; or phenyl or phenylcarbonyl, which can carry one or more same or different substituents, a mono, bi- or tricyclic carbocyclic group containing 7–15 C atoms or a mono-, bi- or tricyclic heterocyclic ring system, $R_7$
signifies hydrogen or alkyl, X
signifies a valency bond, alkylene, carbonyl or carbonylalkylene, $R_8$
signifies alkyl, which can carry one or more same or different substituents selected from hydroxy, alkoxy, amino, alkylamino and dialkylamino, 1,3-dioxolan-4-yl optionally mono- or disubstituted in the 2-position, $PO(R_{11})(R_{12})$ or $PO(OR_{13})(OR_{14})$
and, when X signifies other than a valency bond, $R_8$ also signifies hydroxy, alkoxy, hydroxyalkoxy, alkanoyloxy, alkylcarbonylamino, alkoxycarbonyloxy, alkanoyloxyalkyl, carboxyvinyl, optionally substituted aminoalkanoyloxy, aminoalkylphenyl or aminoalkylbenzoyloxy, alkanoyloxyalkoxy or $NR_9R_{10}$, $R_9$ and $R_{10}$
each individually signify hydrogen or alkyl which can carry one or more same or different substituents selected from hydroxy, alkoxy, amino, alkylamino and dialkylamino,
or $R_9$ signifies hydrogen and $R_{10}$ signifies hydroxy, imidazolin-2-yl or tetrazol-5-yl or $R_9$ and $R_{10}$ together with the nitrogen atom to which they are attached form a heterocyclic ring which is optionally interrupted by nitrogen or oxygen and which can be substituted by alkyl, alkoxy, hydroxy, hydroxyalkyl, oxo, carboxy, aminocarbonyl or alkoxycarbonyl and can be fused with a benzene ring, $R_{11}$ and $R_{12}$
are the same or different and signify alkyl and $R_{13}$ and $R_{14}$
each individually signify hydrogen or alkyl, as well as their tautomers, enantiomers, diastereomers, racemates and physiologically compatible salts or esters and substances which are hydrolyzed or metabolised in vivo to compounds of formula I.

The invention is also concerned with a process for the manufacture of the above compounds, medicaments which contain such compounds and the use of these compounds in the production of medicaments.

Suprisingly, compounds of general formula I are orally active metalloprotein inhibitors, and inhibitors of TNFα synthesis. As such, they have anti-inflammatory activity and are useful in the various disease conditions mentioned above in connection with the pathogenic significance of TNFα. As metalloprotein inhibitors, these compounds have activity in reducing tissue degradation caused by certain metalloproteases and in alleviating the pathological conditions mentioned above in connection with uncontrolled excessive degradation of matrices.

DETAILED DESCRIPTION OF THE INVENTION

The compounds of general formula I which are the object of the invention, will be described in more detail hereinafter. The invention is concerned with compounds of general formula I,

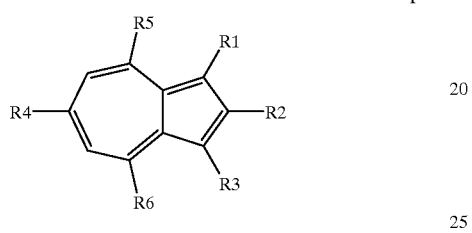

wherein $R_1$ and $R_3$
  each individually signify hydrogen, hydroxy, amino, mercapto, an aliphatic group containing 1–15 carbon atoms, which can carry one or more substituents selected from hydroxy, amino, mercapto, $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, benzyloxy, phenylmercapto, phenyloxy, nitro, cyano, halo, trifluoromethyl, azido, formylamino and phenyl,
  a $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, di-$C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, nitro, cyano, halo, trifluoromethyl or azido group,
  phenyl or phenylcarbonyl, which can carry one or more same or different substituents selected from hydroxy, amino, mercapto, $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, benzyloxy, phenylmercapto, phenyloxy, nitro, cyano, halo, trifluoromethyl, azido, formylamino, carboxy and phenyl, or
  a mono-, bi- or tricyclic carbocyclic group containing 7–15 C atoms or a mono-, bi- or tricyclic heterocyclic ring system, with unsaturated or aromatic carbocycles and heterocycles optionally being partially or completely hydrogenated, $R_2$
  signifies hydrogen, hydroxy, amino, mercapto; an aliphatic group containing 1–15 carbon atoms, which can carry one or more substituents selected from hydroxy, amino, mercapto, $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, benzyloxy, phenylmercapto, phenyloxy, nitro, cyano, halo, trifluoromethyl, azido, formylamino and phenyl,
  a $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, di-$C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, nitro, cyano, halo, trifluoromethyl or azido group,
  phenyl or phenylcarbonyl, which can carry one or more same or different substituents selected from hydroxy, amino, mercapto, $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, benzyloxy, phenylmercapto, phenyloxy, nitro, cyano, halo, trifluoromethyl, azido, formylamino, carboxy and phenyl, or a mono-, bi- or tricyclic carbocyclic group containing 7–15 C atoms or a mono-, bi- or tricyclic heterocyclic heterocyclic ring system, with unsaturated or aromatic carbocycles and heterocycles optionally being partially or completely hydrogenated, $R_4$
signifies $R_8XON(R_7)COCH_2$—, $R_5$ and $R_6$
each individually signify hydrogen, an aliphatic group containing 1–15 carbon atoms, which can carry one or more substituents selected from hydroxy, amino, mercapto, $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, benzyloxy, phenylmercapto, phenyloxy, nitro, cyano, halo, trifluoromethyl, azido, formylamino and phenyl, a $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, di-$C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, nitro, cyano, halo, trifluoromethyl or azido group, phenyl or phenylcarbonyl, which can carry one or more same or different substituents selected from hydroxy, amino, mercapto, $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, benzyloxy, phenylmercapto, phenyloxy, nitro, cyano, halo, trifluoromethyl, azido, formylamino, carboxy and phenyl, or a mono-, bi- or tricyclic carbocyclic residue containing 7–15 C atoms or a mono-, bi- or tricyclic heterocyclic ring system, with unsaturated or aromatic carbocycles and heterocycles optionally being partially or completely hydrogenated, $R_7$
signifies hydrogen or $C_1$–$C_6$-alkyl, X
signifies a valency bond, $C_1$–$C_6$-alkylene, carbonyl or $C_1$–$C_6$-carbonylalkylene, $R_8$
signifies $C_1$–$C_6$-alkyl, which can carry one or more substituents selected from hydroxy, $C_1$–$C_6$-alkoxy, amino, $C_1$–$C_6$-alkylamino and di-$C_1$–$C_6$-alkylamino, 1,3-dioxolan-4-yl optionally mono- or disubstituted in the 2-position, $PO(R_{11})(R_{12})$ or $PO(OR_{13})(OR_{14})$ and, when X signifies other than a valency bond, $R_8$ also signifies hydroxy, $C_1$–$C_6$-alkoxy, hydroxy-$C_1$–$C_6$-alkoxy, $C_1$–$C_6$-alkanoyloxy, $C_1$–$C_6$-alkylcarbonylamino, $C_1$–$C_6$-alkoxycarbonyloxy, $C_1$–$C_6$-alkanoyloxy-$C_1$–$C_6$-alkyl, carboxyvinyl, an optionally N-substituted amino-$C_1$–$C_6$-alkanoyloxy, amino-$C_1$–$C_6$-alkyl-phenyl or amino-$C_1$–$C_6$-alkylbenzoyl group, $C_1$–$C_6$-alkanoyloxy-$C_1$–$C_6$-alkoxy and $NR_9R_{10}$, $R_9$ and $R_{10}$
each individually signify hydrogen, $C_1$–$C_6$-alkyl, which can carry one or more same or different substituents selected from hydroxy, $C_1$–$C_6$-alkoxy, amino, $C_1$–$C_6$-alkylamino and di-$C_1$–$C_6$-alkylamino, or $R_9$ signifies hydrogen and $R_{10}$ signifies hydroxy, imidazolin-2-yl or tetrazol-5-yl or $R_9$ and $R_{10}$ together with the nitrogen atom to which they are attached form a heterocyclic ring which is optionally interrupted by nitrogen or oxygen and which can be substituted by $C_1$–$C_6$-alkyl, $C_1$–$C_6$-alkoxy, hydroxy, hydroxy-$C_1$–$C_6$-alkyl, oxo, carboxy, aminocarbonyl or $C_1$–$C_6$-alkoxycarbonyl and can be fused with a benzene ring, $R_{11}$ and $R_{12}$
are the same or different and signify $C_1$–$C_6$-alkyl, and $R_{13}$ and $R_{14}$
each individually signify hydrogen or $C_1$–$C_6$-alkyl, as well as their tautomers, enantiomers, diastereomers, racemates and physiologically compatible salts or esters and substances which are hydrolyzed or metabolised in vivo to compounds of formula I.

Valency bond signifies a covalent single bond.

The following defines the various groups of formula I. Many groups contain substitutions on individual groups as defined below, for example alkylamino being alkyl as defined below bonded to an amino group, or alkynyl as defined below bonded to an oxygen. Other groups are combinations of individual groups defined below, for example carbonylalkylene, or alkoxycarbonylalkyl. Still other groups contain substitutions on the combined groups, for example alkenyloxycarbonyl, or alkylaminocarbonyl or alkenylaminocarbonyl. The groups of formula I are attached by the left-hand group, such that aminoalkylphenyl is attached by the phenyl while alkylcarbonylamino is attached by the amino. An alkynyl group is a partially unsaturated hydrocarbon chain containing at least one triple bond, which is preferably 2–15 and more preferably 2–10 carbons in length.

Halo is halogen, i.e. bromine, chlorine, fluorine or iodine.

An alkyl group is a saturated hydrocarbon chain preferably 1–15 and more preferably 1–10 carbons in length. Examples are methyl, ethyl, propyl, isopropyl, butyl, sec-butyl, tert-butyl, pentyl, hexyl, heptyl, octyl, nonyl, and decyl.

An alkenyl group is a nonaromatic partially unsaturated hydrocarbon chain containing at least one double bond, which is preferably 2–15 and more preferably 2–10 carbons in length. Examples are vinyl, allyl, dimethylallyl, butenyl, isobutenyl, pentenyl.

An alkynyl group is a nonaromatic partially unsaturated hydrocarbon chain containing at least one triple bond, which is preferably 2–15 and more preferably 2–10 carbons in length. Examples are ethynyl or propynyl.

An alkoxy group is a lower alkyl as defined above which is bonded by an oxygen to another group. Examples are methoxy, ethoxy, propyloxy, isopropyloxy, butyloxy, sec-butyloxy, tert-butyloxy.

A cyclic alkyl or alkenyl group is a nonaromatic hydrocarbon ring which is preferably 3–15 and more preferably 3–8 carbons in length, and which is saturated (alkyl) or contains one or more double(alkenyl) bonds. Examples are cyclopropyl, cyclobutyl, cyclopentyl and cyclohexyl; cyclopentenyl, cyclohexenyl, cycloheptenyl and cyclooctenyl.

An alkylene is a saturated hydrocarbon chain which links together two other groups. Examples are methylene, 1,1-ethylene, 1,2-ethylene, 1,1-propylene, 1,2-propylene, 1,3-propylene, 1,1-butylene, 1,2-butylene, 1,3-butylene, 1,4-butylene, 1,1-pentylene and 1,1-hexylene. A carbonylalkylene group present as X in the residue $R^4$ signifies that the alkylene moiety is connected to the O atom, while the carbonyl moiety is converted to $R_8$.

Similarly, alkylcarbonylamino, hydroxyalkoxy and alkanoyloxy are all connected via the their terminal group, viz. "-amino", "-oxy" and "-oxy", respectively.

An aliphatic group is a straight-chain, branched-chain or cyclic alkyl, alkenyl or alkynyl group containing 1–15, preferably 1–10, carbon atoms, which may or may not be substituted, such as e.g. methyl, ethyl, propyl, isopropyl, butyl, sec-butyl, tert-butyl, pentyl, hexyl, heptyl, octyl, nonyl, decyl, cyclopropyl, cyclobutyl, cyclopentyl and cyclohexyl. Unsaturated groups are e.g. vinyl, allyl, dimethylallyl, butenyl, isobutenyl, pentenyl, ethynyl or propynyl.

A $C_1$–$C_6$-alkyl group in $C_1$–$C_6$-alkyl, $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_1$–$C_6$-alkylcarbonylamino, $C_1$–$C_6$-alkylaminocarbonyl, $C_1$–$C_6$-alkoxycarbonyl, carboxy-$C_1$–$C_6$-alkyl, $C_1$–$C_6$-alkyloxycarbonyl-$C_1$–$C_6$-alkyl, $C_2$–$C_6$-alkenyloxy-carbonyl-$C_1$–$C_6$-alkyl, $C_2$–$C_6$-alkynyloxycarbonyl-$C_1$–$C_6$-alkyl, $C_1$–$C_6$-alkanoyloxy, $C_1$–$C_6$-alkoxycarbonyloxy, $C_1$–$C_6$-alkoxy-$C_1$–$C_6$-alkyl, $C_1$–$C_6$-alkanoyloxy-$C_1$–$C_6$-alkyl, amino-$C_1$–$C_6$-alkanoyloxy, amino-$C_1$–$C_6$-alkyl-phenyl, amino-$C_1$–$C_6$-alkyl-benzoyl, $C_1$–$C_6$-alkanoyloxy-$C_1$–$C_6$-alkoxy or hydroxy-$C_1$–$C_6$-alkyl signifies straight-chain, branched-chain or cyclic groups, preferably methyl, ethyl, propyl, isopropyl, butyl, sec- or tert-butyl, pentyl, hexyl, cyclopropyl, cyclobutyl, cyclopentyl, cyclohexyl ($C_{1-6}$-alkyl), methoxy, ethoxy, propyloxy, isopropyloxy, butyloxy, sec-butyloxy, tert-butyloxy ($C_{1-6}$-alkoxy), methoxycarbonyl, ethoxycarbonyl, propyloxycarbonyl, butyloxycarbonyl ($C_{1-6}$-alkylcarbonyl), carboxymethyl, carboxyethyl, carboxypropyl(carboxy-$C_{1-6}$-alkyl), methoxycarbonylethyl, ethoxycarbonylethyl, methoxycarbonylpropyl, ethoxycarbonylpropyl ($C_{1-6}$-alkoxycarbonyl-$C_{1-6}$-alkyl), carboxymethoxy, carboxyethoxy, carboxypropyloxy(carboxy-$C_{1-6}$-alkoxy), methoxycarbonylmethoxy, ethoxycarbonylethoxy, propoxycarbonylmethoxy, methoxycarbonylethoxy, ethoxycarbonylethoxy ($C_{1-6}$-alkoxycarbonyl-$C_{1-6}$-alkoxy), aminomethyl, aminoethyl, aminopropyl(amino-$C_{1-6}$-alkyl), methylmercapto, ethylmercapto and propylmercapto ($C_{1-6}$-alkylmercapto).

The $C_2$–$C_6$-alkenyl and $C_2$–$C_6$-alkynyl groups in $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_2$–$C_6$-alkenyloxycarbonyl, $C_2$–$C_6$-alkynyloxycarbonyl, $C_2$–$C_6$-alkenyloxycarbonyl-$C_1$–$C_6$-alkyl, $C_2$–$C_6$-alkynyloxycarbonyl-$C_1$–$C_6$-alkyl are straight-chain, branched-chain or cyclic groups. Vinyl, propenyl, butenyl, pentenyl, hexenyl ($C_2$–$C_6$-alkenyl), ethynyl, propargyl ($C_2$–$C_6$-alkynyl), vinyloxy, allyloxy ($C_2$–$C_6$-alkenyloxy), propargyloxy ($C_2$–$C_6$-alkynyloxy), allyloxycarbonyl ($C_2$–$C_6$-alkenyloxycarbonyl), propargyloxycarbonyl ($C_2$–$C_6$-alkynyloxycarbonyl), allyloxycarbonylmethyl, allyloxycarbonylethyl, allyloxycarbonylpropyl ($C_2$–$C_6$-alkenyloxycarbonyl-$C_1$–$C_6$-alkyl), propargyloxycarbonylmethyl, propargyloxycarbonylethyl and propargyloxycarbonylpropyl ($C_2$–$C_6$-alkynyloxycarbonyl-$C_1$–$C_6$-alkyl) are preferred.

A carbocyclic group containing 7–15 C atoms can be mono-, bi- or tricyclic (i.e. one, two, or three rings)and can have 5–7 carbon atoms in each ring. This ring can be aromatic or partly or wholly saturated. Naphthyl, anthracenyl, phenanthrenyl, fluorenyl, indenyl, acenaphthylenyl, norbornyl, adamantyl, $C_3$–$C_7$-cycloalkyl or $C_5$–$C_8$-cycloalkenyl are preferred. Furthermore, the carbocyclic ring can carry 1–3 substituents selected from an aliphatic group containing 1–9 carbon atoms, hydroxy, amino, mercapto, $C_1$–$C_6$-alkoxy, $C_1$–$C_6$-alkylamino, di-$C_{1-6}$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, $C_1$–$C_6$-alkylaminocarbonyl, carbonyl, $C_1$–$C_6$-alkylcarbonyl, carboxyl, $C_1$–$C_6$-alkoxycarbonyl, $C_2$–$C_6$-alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, benzyloxy, phenylmercapto, phenyloxy, nitro, cyano, halo, trifluoromethyl, azido, formylamino and phenyl.

Alkylene groups in $C_1$–$C_6$-alkylene and $C_1$–$C_6$-alkylenecarbonyl are, for example, methylene, 1,1-ethylene, 1,2-ethylene, 1,1-propylene, 1,2-propylene, 1,3-propylene, 1,1-butylene, 1,2-butylene, 1,3-butylene, 1,4-butylene, 1,1-pentylene and 1,1-hexylene.

Under a mono-, bi- or tricyclic heterocyclic ring system there is to be understood a saturated or unsaturated ring system with one, two, or three rings, each ring having five- to seven-members which contain 1–4 same or different hetero atoms such as nitrogen, oxygen or sulphur, such as e.g. the pyridine, pyrimidine, pyridazine, pyrazine, triazine, pyrrole, pyrazole, piperidine, morpholine, imidazole, triazole, thiazole, oxazole, isoxazole, oxadiazole, furazan, furan, thiophene, indole, quinoline, isoquinoline, coumarone, thionaphthene, benzoxazole, benzthiazole, indazole, benzimidazole, benztriazole, chromene, phthalazine, quinazoline, quinoxaline, methylenedioxybenzene, carbazole, acridine, phenoxazine, phenothiazine, phenazine or purine system, with the unsaturated or aromatic carbocycles and heterocycles optionally being partly or completely hydrogenated. Furthermore, the heterocyclic system can carry one or more same or different substituents selected from an aliphatic group containing 1–9 carbon atoms, hydroxy, amino, mercapto, $C_1$–$C_6$-alkoxy, $C_1$–$C_6$-alkylamino, di-$C_1$–$C_6$-alkylamino, $C_1$–$C_6$-alkylmercapto, $C_1$–$C_6$-alkylsulphinyl, $C_1$–$C_6$-alkylsulphonyl, $C_2$–$C_6$-alkenyl, $C_2$–$C_6$-alkynyl, $C_2$–$C_6$-alkenyloxy, $C_2$–$C_6$-alkenylmercapto, $C_2$–$C_6$-alkynyloxy, $C_2$–$C_6$-alkynylmercapto, $C_1$–$C_6$-alkylcarbonylamino, $C_1$–$C_6$-alkylaminocarbonyl, formyl, $C_1$–$C_6$-alkylcarbonyl, carboxyl, $C_1$–$C_6$-alkoxycarbonyl, $C_2$–$C_6$- alkenyloxycarbonyl, $C_2$–$C_6$-alkynyloxycarbonyl, carboxy-$C_1$–$C_6$-alkyl, $C_1$–$C_6$-alkyloxycarbonyl-$C_1$–$C_6$-alkyl, $C_2$–$C_6$-alkenyloxycarbonyl-$C_1$–$C_6$-alkyl, $C_2$–$C_6$-alkynyloxycarbonyl-$C_1$–$C_6$-alkyl, benzyloxy, phenylmercapto, phenyloxy, nitro, cyano, halo, trifluoromethyl, azido, formylamino and phenyl. Pyrrolidine, piperidine, piperazine, morpholine, hexahydroazepine, tetrahydrofuran, tetrahydropyran, tetrahydrothiophene, 4,5-dihydroimidazole, pyrrole, imidazole, pyrazine, pyrimidine, pyridazine, 1H-azepine, 3H-azepine, 1,2-diazepine, 1,4-diazepine, furan, thiophene, oxazole, isoxazole, thiazole, isothiazole, pyrazole, pyrrolidinone, imidazolidinone, piperidinone, indole, purine, quinoline and isoquinoline are preferred.

Preferred compounds of general formula I are those in which $R_1$ and/or $R_3$ signify hydrogen or $C_1$–$C_6$-alkoxycarbonyl, $R_2$ signifies hydrogen, amino, $C_1$–$C_6$-alkylcarbonylamino, di-$C_1$–$C_6$-alkylcarbonylamino, $R_5$ and $R_6$ signify hydrogen or $C_1$–$C_6$-alkoxy, $R_7$ signifies hydrogen or $C_1$–$C_6$-alkyl, X signifies a valency bond, $C_1$–$C_6$-alkylene, carbonyl or $C_1$–$C_6$-carbonylalkylene, $R_8$ signifies $C_1$–$C_6$-alkyl, which can be substituted by one or more same or different substituents selected from hydroxy, $C_1$–$C_6$-alkoxy, amino, $C_1$–$C_6$-alkylamino and di-$C_1$–$C_6$-alkylamino, 2,2-di-$C_1$–$C_6$-alkyl-1,3-dioxolan-4-yl or $PO(OR_{13})(O_{14})$, and, when X signifies other than a valency bond, $R_8$ also signifies hydroxy, $C_1$–$C_6$-alkoxy, hydroxy-$C_1$–$C_6$-alkoxy or $NR_9R_{10}$ in which $R_9$ and $R_{10}$ signify hydrogen, $C_1$–$C_6$-alkyl, which can carry one or more same or different substituents selected from hydroxy and $C_1$–$C_6$-alkoxy, or $R_9$ and $R_{10}$ together with the nitrogen atom to which they are attached form a heterocyclic ring which is optionally interrupted by nitrogen or oxygen and which can be substituted by $C_1$–$C_6$-alkyl, $C_1$–$C_6$-alkoxy, hydroxy, hydroxy-$C_1$–$C_6$-alkyl, oxo, carboxy, aminocarbonyl or $C_1$–$C_6$-alkoxycarbonyl and fused with a benzene ring and $R_{13}$ and $R_{14}$ are the same or different and signify hydrogen or $C_1$–$C_6$-alkyl.

Especially preferred substituent values are methoxycarbonyl, ethoxycarbonyl and tbutoxycarbonyl, particularly ethoxycarbonyl, for $R_1$ and/or $R_3$, amino for $R_2$, hydrogen for $R_5$ and $R_6$, hydrogen or methyl for $R_7$, carbonylmethylene, ethylene or a valency bond for X, 2,3-dihydroxypropyl, 2-hydroxy-3-methoxypropyl, 2,2-dimethyl-1,3-dioxolan-4-yl, 3-dimethylamino-2-hydroxypropyl or, where X signifies other than a valency bond, also hydroxy, ethoxy or $NR_{90}R_{100}$, for $R_8$, with $R_{90}$ and $R_{100}$ each individually signifying methoxyethyl, methyl or hydroxyethyl or $R_{90}$ and $R_{100}$ together with the nitrogen atom forming a pyrrolidine, piperidine or morpholine ring.

Under the physiologically compatible salts of the compounds of general formula I there are to be understood, for example, formates, acetates, caproates, oleates, lactates or salts of carboxylic acids containing up to 18 carbon atoms or salts of dicarboxylic acids and tricarboxylic acids such as citrates, malonates and tartrates or alkanesulphonates containing up to 10 carbon atoms or p-toluenesulphonates or salicylates or trifluoroacetates or salts of physiologically compatible mineral acids such as hydrochloric acid, hydrobromic acid, hydroiodic acid, sulphuric acid or phosphoric acid. The compounds of formula I which have a free carboxyl group can also form salts with physiologically compatible bases. Examples of such salts are alkali metal, alkaline earth metal, ammonium and alkylammonium salts, such as the sodium, potassium, calcium or tetramethylammonium salt.

Pure enantiomers of the compounds of formula I can be obtained either by racemate resolution (via salt formation with optically active acids or bases) or by using optically active starting materials in the synthesis.

The compounds of formula I can be solvated, especially hydrated. The hydration can be effected in the course of the manufacture or can occur gradually as a result of hygroscopic properties of an initially anhydrous compound of formula I.

This invention is also directed to a pharmaceutical preparation containing a compound of claim 1 and a therapeutically inert carrier, particularly for the treatment and prophylaxis of inflammatory diseases, and to a method for treatment of inflammatory disease which comprises administering to an affected patient a compound of claim 1 and a pharmaceutically acceptable carrier in an amount effective for treatment of the inflammatory disease.

Compounds of formula I can be administered in liquid or solid form or in the form of aerosols orally, enterally, parenterally, topically, nasally, pulmonally or rectally in all usual non-toxic pharmaceutically acceptable carrier materials, adjuvants and additives. The term "parentally" embraces subcutaneous, intravenous and intramuscular injection or infusion. Oral administration forms are described e.g. in W. A. Ritschel, Die Tablette, 1996, Aulendorf, and can be e.g. tablets, capsules, dragées, syrups, solutions, suspensions, emulsions, elixirs etc., which can contain one of more additives from the following groups, such as e.g. flavorants, sweeteners, colorants and preservatives. Oral administration forms contain the active ingredient together with non-toxic, pharmaceutically acceptable carrier materials which are suitable for the production of tablets, capsules, dragées etc., such as e.g. calcium carbonate, sodium carbonate, lactose, calcium phosphate or sodium phosphate; starch, mannitol, methylcellulose, talc, highly dispersible silicic acids, high molecular weight fatty acids (such as stearic acid), ground nut oil, olive oil, paraffin, miglyol, gelatine, agar—agar, magnesium stearate, beeswax, cetyl alcohol, lecithin, glycerol, animal and vegetable fats and solid high molecular weight polymers (such as polyethylene glycols). Tablets, capsules, dragees etc. can be provided with an appropriate coating, such as e.g. glyceryl monostearate or glyceryl distearate, in order to prevent undesired side effects in the stomach or to provide a longer duration of activity by delayed absorption in the gastrointestinal tract. Preferred injection media which are used are sterile injectable aqueous or oily solutions or suspensions which contain the usual additives, such as stabilizers and solubilizers. Such additives can be e.g. water, isotonic saline, 1,3-butanediol, fatty acids (such as oleic acid), mono- and diglycerides or miglyol. For rectal administration there can be used all suitable non-irritant additives which are solid at normal temperatures and which are liquid at the rectal temperature, such as e.g. cocoa butter and polyethylene glycol. Conventional pharmaceutical carrier media are used for administration as aeosols. Creams, tinctures, gels, solutions or suspensions etc. containing Conventional pharmaceutical additives are used for external application.

The dosage can depend on various factors, such as the mode of administration, species, age and/or individual condition. The daily dosage of active substance to be administered lies at 0.01 mg to approximately 100 mg/kg body weight, preferably at 0.1 to 10 mg/kg body weight , and can be administered in one dose or in several divided doses.

The manufacture of the compounds of formula I is effected according to methods which are known per se and which are described in the literature (e.g. in standard works such as Houben-Weyl, Methoden der Organischen Chomie, Georg Thieme Verlag, Stuttgart; Organic Reactions, John Wiley & Sons Inc., New York) using reaction conditions which are known and suitable for the respective reactions and which are also described in EP 97110533.3. Use can also be made of variants which are known per se, but not referred to in more detail herein. Furthermore, a compound of formula I can be converted into a different compound of formula I according to methods known per se.

The process in accordance with the invention for the manufacture of compounds of formula I comprises a) reacting a compound of formula I in which $R_1$, $R_2$, $R_3$, $R_5$ and $R_6$ have the given significance and $R_4$ signifies $HON(R_7)COCH_2—$, wherein $R_7$ has the given significance, or an alkali metal or alkaline earth metal salt thereof, with a compound yielding the group $R_8—X—$, wherein X and $R_8$ have the given significance, or b) reacting a compound of formula I in which $R_4$ signifies carboxymethyl or a reactive group derived therefrom with a compound $R_8XON(R_7)H$, wherein X, $R_7$ and $R_8$ have the significance given above, and subsequently, if desired, converting the compound of formula I obtained into a different compound of formula I defined by the claim and, desired, converting a compound of formula I into a pharmacologically compatible salt.

As compounds yielding the group $R_8—X—$ there come into consideration in accordance with the above alternative a) e.g. compounds $R_8—X—Y$ in which X and $R_8$ have the given significance and Y signifies a residue which participates as a leaving group in alkylation or acylation reactions, such as, for example, halogen (preferably chlorine or bromine), azido, alkoxy, aryloxy, alkylthio, arylthio, acyloxy, imidazolyl, mesyloxy, tosyloxy or brosyloxy and inorganic groups such as, for example, sulphate and phosphate. Y can also represent an alcoholic hydroxy group, in which case the reaction is carried out in the presence of a water-withdrawing agent, such as dicyclohexylcarbodiimide or N,N'-carbonyldiimidazole.

An amine $R_8H$ is combined with N,N'-carbonyldiimidazole for the introduction of carbamoyl groups $R_8—X—$ (see Example 33). If desired, the corresponding isocyanate can be used (see Example 29).

The reaction is conveniently effected in a solvent such as a lower alcohol, for example methanol, ethanol, propanol or isopropanol, or an ether such as diethyl ether or tetrahydrofuran or dimethylformamide, dimethyl sulphoxide or dimethylacetamide or in a mixture of the aforementioned solvents at temperature between 0° C. and the boiling point of the solution, optionally in the presence of a base such as, for example, sodium hydroxide or potassium carbonate, an alkali alcoholate or a tertiary amine.

Compounds $R_8—X—Y$ and $R_8—XON(R_7)H$ are known from the literature or can be prepared from commercially available materials according to processes from the literature. Diethyl 2-amino-6-[(hydroxycarbamoyl)-methyl]-azulene-1,3-dicarboxylate is known from EP 97110533.3.

Preferred in the scope of the present invention are the following compounds as well as the compounds named in the Examples and compounds derived by a combination of all substituent meanings set forth in the claims:

Compounds of the formula

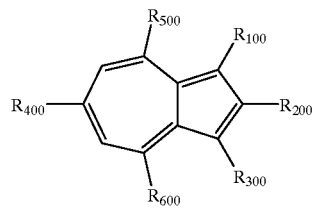

Ia wherein $R_{100}$ and $R_{300}$
 each independently signify hydrogen or $C_1$–$C_6$-alkoxycarbonyl, $R_{200}$
 signifies hydrogen, amino, $C_1$–$C_6$-alkylcarbonylamino or di-$C_1$–$C_6$-alkylcarbonylamino, $R_{400}$
 signifies $R_{800}XON(R_7)COCH_2—$, $R_{500}$ and $R_{600}$
 each independently signify hydrogen or $C_{1\text{-}6}$-alkoxy, $R_7$
 signifies hydrogen or $C_1$–$C_6$-alkyl, X
 signifies a valency bond, $C_1$–$C_6$-alkylene, carbonyl or $C_1$–$C_6$-carbonylalkylene, $R_{800}$
 signifies $C_1$–$C_6$, which can be substituted by one or more same or different substituents selected from hydroxy, amino, $C_1$–$C_6$-alkylamino and di-$C_1$–$C_6$-alkylamino, 2,2-di-$C_1$–$C_6$-alkyl-1,3-dioxolan-4-yl or $PO(OR_{13})(OR_4)$, and, when X signifies other than a valency bond, $R_{800}$ also signifies hydroxy, $C_1$–$C_6$-alkoxy, hydroxy-$C_1$–$C_6$-alkyl or $NR_{900}R_{1000}$, $R_{900}$ and $R_{1000}$
 each individually signify hydrogen, $C_1$–$C_6$-alkyl, which can carry one or more same or different substituents selected from hydroxy, $C_1$–$C_6$-alkoxy and amino or $R_{900}$ and $R_{1000}$ together with the nitrogen atom to which they are attached form a heterocyclic ring which is optionally interrupted by nitrogen or oxygen and which can be substituted by $C_1$–$C_6$-alkyl, $C_1$–$C_6$-alkoxy, hydroxy, hydroxy-$C_1$–$C_6$-alkyl, oxo, carboxy, aminocarbonyl or $C_1$–$C_6$-alkoxycarbonyl and can be fused with a benzene ring, and $R_{13}$ and $R_{14}$
 each individually signify hydrogen or $C_1$–$C_6$-alkyl, as well as their tautomers, enantiomers, diastereomers, racemates and physiologically compatible salts or esters and substances which are hydrolyzed or metabolised in vivo to compounds of formula 1a.

Compounds of the formula

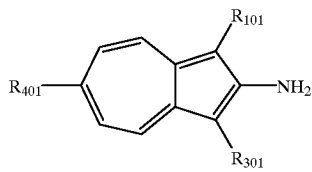

Ib wherein $R_{101}$ and $R_{301}$
signify $C_1$–$C_6$-alkoxycarbonyl, $R_{401}$
signifies $R_{801}XON(R_7)COCH_2$—, $R_7$
signifies hydrogen or $C_1$–$C_6$-alkyl, X
signifies a valency bond, $C_1$–$C_6$-alkylene, carbonyl or $C_1$–$C_6$-carbonylalkylene, $R_{801}$
signifies $C_1$–$C_6$, which can be substituted by one or more same or different substituents selected from hydroxy, amino, $C_1$–$C_6$-alkylamino and di-$C_1$–$C_6$-alkylamino, 2,2-di-$C_1$–$C_6$-alkyl-1,3-dioxolan-4-yl or $PO(OR_{13})(OR_4)$, and, when X signifies other than a valency bond, $R_{801}$ also signifies hydroxy, $C_1$–$C_6$-alkoxy or $NR_{901}R_{1001}$, $NR_{901}$ and $R_{1001}$
each individually signify hydrogen, $C_1$–$C_6$-alkyl, which can carry one or more same or different substituents selected from hydroxy, $C_1$–$C_6$-alkoxy and amino or $R_{901}$ and $R_{1001}$ together with the nitrogen atom to which they are attached form a heterocyclic ring which is optionally interrupted by nitrogen or oxygen and which can be substituted by $C_1$–$C_6$-alkyl, and $R_{13}$ and $R_{14}$
each individually signify hydrogen or $C_1$–$C_6$-alkyl, as well as their tautomers, enantiomers, diastereomers, racemates and physiologically compatible salts or esters and substances which are hydrolyzed or metabolised in vivo to compounds of formula Ib.

Compounds of the formula

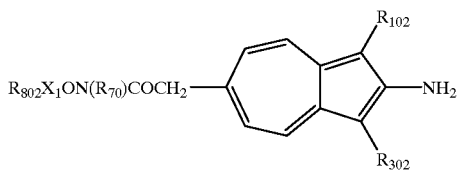

Ic wherein $R_{102}$ and/or $R_{302}$
signify methoxycarbonyl, ethoxycarbonyl or tbutoxycarbonyl, particularly ethoxycarbonyl, $R_{70}$
signifies hydrogen or methyl, $X_1$ signifies carbonylmethylene, ethylene or a valency bond, $R_{802}$
signifies 2,3-dihydroxypropyl, 2-hydroxy-3-methoxypropyl, 2,2-dimethyl-1,3-dioxolan-4-yl, 3-dimethylamino-2-hydroxypropyl or, where $X_1$ signifies other than a valency bond, also hydroxy, ethoxy or —$NR_{902}R_{1002}$, $R_{902}$ and $R_{1002}$
each individually signify methoxyethyl, methyl or hydroxyethyl or $R_{902}$ and $R_{1002}$ together with the nitrogen atom form a pyrrolidine, piperidine or morpholine ring, as well as their tautomers, enantiomers, diastereomers, racemates and physiologically compatible salts or esters and substances which are hydrolyzed or metabolised in vivo to compounds of formula Ic.

Diethyl 2-amino-6-[(dimethyl-phosphinoylmethoxycarbamoyl)-methyl]-azulene-1,3-dicarboxylate;

diethyl 2-amino-6-[(diethoxy-phosphoryloxycarbamoyl)-methyl]-azulene-1,3-dicarboxylate;

diethyl 2-amino-6-[(2,2-dimethyl-propanoyloxy)-methoxycarbamoyl-methyl]-azulene-1,3-dicarboxylate;

diethyl 2-amino-6-(ethoxymethoxycarbamoyl-methyl)-azulene-1,3-dicarboxylate;

diethyl 2-amino-6-[(3-hydroxy-propoxycarbamoyl)-methyl]-azulene-1,3-dicarboxylate;

diethyl 2-amino-6-{[2-(dimethyl-phosphinoyl)-ethoxycarbamoyl]-methyl}-azulene-1,3-dicarboxylate;

diethyl 2-amino-6-[(1-pyrrolidin-1-yl-ethoxycarbamoyl)-methyl]-azulene-1,3-dicarboxylate;

diethyl 2-amino-6-[(1-ethoxy-1-methyl-ethoxycarbamoyl)-methyl]-azulene-1,3-dicarboxylate;

diethyl 2-amino-6-[(3-pyrrolidin-1-yl-propoxycarbamoyl)-methyl]-azulene-1,3-dicarboxylate;

diethyl 2-amino-6-{[3-(1,3-dioxo-1,3-dihydro-isoindol-2-yl)-propoxycarbamoyl]-methyl}-azulene-1,3-dicarboxylate;

diethyl 2-amino-6-[(pyrrolidin-1-ylcarbonyloxycarbamoyl)-methyl]-azulene-1,3-dicarboxylate;

diethyl 2-amino-6-[(2-hydroxy-ethoxycarbonylmethoxycarbamoyl)-methyl]-azulene-1,3-dicarboxylate;

diethyl 2-amino-6-(carboxymethoxycarbamoyl-methyl)-azulene-1,3-dicarboxylate;

diethyl 2-amino-6-{[(4,5-dihydro-1H-imidazol-2-ylcarbamoyl)-methoxycarbamoyl]-methyl}-azulene-1,3-dicarboxylate;

diethyl 2-amino-6-{[(1H-tetrazol-5-ylcarbamoyl)-methoxycarbamoyl]-methyl}-azulene-1,3-dicarboxylate;

diethyl 2-amino-6-(hydroxycarbamoylmethoxycarbamoyl-methyl)-azulene-1,3-dicarboxylate;

diethyl 2-amino-6-[(4-hydroxy-butoxycarbamoyl)-methyl]-azulene-1,3-dicarboxylate;

diethyl 2-amino-6-{[2-(2-hydroxy-ethoxy)-ethoxycarbamoyl]-methyl}-azulene-1,3-dicarboxylate;

diethyl 2-amino-6-{[2-(1,3-dioxo-1,3-dihydro-isoindol-2-yl)-ethoxycarbamoyl]-methyl}-azulene-1,3-dicarboxylate;

diethyl 2-amino-6-{[(dimethyl-phosphinoylmethoxy)-methyl-carbamoyl]-methyl}-azulene-1,3-dicarboxylate;

diethyl 2-amino-6-[(methyl-phosphonomethoxy-carbamoyl)-methyl]-azulene-1,3-dicarboxylate;

diethyl 2-amino-6-{[(diethoxy-phosphorylmethoxy)-methyl-carbamoyl]-methyl}-azulene-1,3-dicarboxylate;

diethyl 2-amino-6-{[methyl-(3-pyrrolidin-1-yl-propoxy)-carbamoyl]-methyl}-azulene-1,3-dicarboxylate;

diethyl 2-amino-6-({[3-(1,3-dioxo-1,3-dihydro-isoindol-2-yl)-propoxy]-methyl-carbamoyl}-methyl)-azulene-1,3-dicarboxylate;

diethyl 2-amino-6-{[methyl-(2-oxo-2-pyrrolidin-1-yl-ethoxy)-carbamoyl]-methyl}-azulene-1,3-dicarboxylate;

diethyl 2-amino-6-[(ethoxycarbonylmethoxy-methyl-carbamoyl)-methyl]-azulene-1,3-dicarboxylate;
diethyl 2-amino-6-[(carboxymethoxy-methyl-carbamoyl)-methyl]-azulene-1,3-dicarboxylate;
diethyl 2-amino-6-[(hydroxycarbamoylmethoxy-methyl-carbamoyl)-methyl]-azulene-1,3-dicarboxylate;
diethyl 2-amino-6-{[(2-ethoxy-ethoxy)-methyl-carbamoyl]-methyl}-azulene-1,3-dicarboxylate;
diethyl 2-amino-6-({[2-(2-hydroxy-ethoxy)-ethoxy]-methyl-carbamoyl}-methyl)-azulene-1,3-dicarboxylate;
diethyl 2-amino-6-{([(2-hydroxy-ethoxy)-methyl-carbamoyl]-methyl}-azulene-1,3-dicarboxylate;
diethyl 2-amino-6-({[2-(1,3-dioxo-1,3-dihydro-isoindol-2-yl)-ethoxy]-methyl-carbamoyl}-methyl)-azulene-1,3-dicarboxylate;
diethyl 2-amino-6-{[ethyl-(2-oxo-2-pyrrolidin-1-yl-ethoxy)-carbamoyl]-methyl}-azulene-1,3-dicarboxylate;
diethyl 2-amino-6-({[(4,5-dihydro-1H-imidazol-2-ylcarbamoyl)-methoxy]-ethyl-carbamoyl}-methyl)-azulene-1,3-dicarboxylate; and
diethyl 2-amino-6-({[2-(1,3-dioxo-1,3-dihydro-isoindol-2-yl)-ethoxy]-ethyl-carbamoyl}-methyl)-azulene-1,3-dicarboxylate.

As mentioned, the compounds of general formula I are orally available inhibitors of metalloproteins. They inhibit TNFα synthesis, which means inhibition of an antiinflammatory activity in the case of corresponding disease symptoms. The TNFα synthesis inhibition was demonstrated not only in vitro, but also in vivo according to the following experimental procedures:

Experimental Procedure in Vitro

TNFα Synthesis Assay

Human leukocytes are obtained from heparinized full blood over a Ficol gradient, washed with RPMI 1640 medium having the prescribed additives and adjusted in the same medium to a cell count of $1 \times 10^6$ cells/ml. 20 µl of the substance to be tested in 10-fold concentration, 20 µl of an LPS solution of 4 µg/ml and 160 µl of the adjusted cell suspension are incubated in the individual wells of a 96 well culture plate at 37° C. for 2 hours. The experiments are carried out as double determinations. At the end of the incubation period the plates are carefully shaken and centrifuged. Two samples each of 50 µl are withdrawn from the clear culture supernatant for the analysis of TNFα.

Analysis of TNFα in the Cell Cupernatant by Enzyme Immunoassay

Nunc-Maxisorb plates are coated with a mouse-anti-human-TNFα antibody (1 µg/ml, 50 µl/well, Dianova/Pharmingen 18631D, carbonate buffer pH 9.5) and free binding capacity is saturated with a gelatine- and serum albumin-containing blocking buffer. After washing the plates there are pipetted in in double determination in each case 25 µl of the analyte as well as on each plate a series of standard concentrations. For the detection of the analyte, 25 µl of a biotinylated mouse-anti-human-TNFα antibody (4 µl/ml 25 µl/well, Dianova/Pharmingen 18642D, blocking buffer) are added and the plates are shaken at room temperature for 2 hours. After washing incubation is carried out with streptavidin-alkaline phosphatase conjugate (50 µl/well) and finally with 4-nitrophenyl phosphate and evaluation is carried out on a photometer. The concentrations of the measured samples are determined using a computer program based on a calibration curve from the co-determined standard concentrations.

Determination of the $IC_{50}$

The percentage inhibition for the individual sample is calculated by comparing the TNFα concentration obtained for the measured samples with the non-inhibited samples. The $IC_{50}$ is determined by computer from the concentration relationship of the inhibitor value.

Experimental Procedure in Vivo 15 minutes prior to the intraperitoneal injection of 700 mg/kg of D-galactosamine (DGaIN) and 70 µg/kg of lipopolysaccharide (LPS) the indicated test substances are administered intraperitoneally or orally to NMRI-mice. 90 minutes after the injection of DGaIN/LPS blood is removed from the animal and the serum obtained therefrom is freeze-dried for the analysis of TNFα by enzyme inmunoassay (EIA). The EIA is carried out analogously to that described above. However, anti-mouse TNFα antibodies are used.

Results:

| Example number | TNFα synthesis inhibition | |
|---|---|---|
| | in vitro $IC_{50}$ (µg/ml) | in vivo active dosage (mg/kg) |
| 4 | 0.03 | 30 i.p. |
| | | 30 p.o. |
| 20 | 0.05 | 10 i.p. |
| | | 40 p.o. |
| 31 | 0.1 | 20 i.p. |
| | | 60 p.o. |

The following Examples illustrate the invention, but are not limiting:

EXAMPLE 1

Diethyl 2-amino-6-[(2-oxo-2-piperidin-1-yl-ethoxycarbamoyl)-methyl]-azulene-1,3-dicarboxylate.

A mixture of 0.96 g (2.5 mmol) of diethyl 2-amino-6-[(hydroxycarbamoyl)-methyl]-azulene-1,3-dicarboxylate sodium, 50 ml of methanol, 0.4 g (2.5 mmol) of N-chloroacetyl-piperidine and 20 mg of sodium iodide is heated at reflux for 20 hours. Thereafter, the mixture is concentrated and the residue is chromatographed on silica gel. Elution with isohexane: ethyl acetate 1:1 gives 0.42 g (35% of theory) of the title compound of m.p. 153–155° C.

EXAMPLE 2

Diethyl 2-amino-6-[(2-oxo-2-pyrrolidin-1-yl-ethoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and N-chloroacetyl-pyrrolidine the title compound of m.p. 168–170° C. is obtained in 24% yield.

EXAMPLE 3

Diethyl 2-amino-6-[(2-oxo-2-morpholin-4-yl-ethoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and N-chloroacetyl-morpholine the title compound of m.p. 196–198° C. is obtained in 33% yield.

EXAMPLE 4

Diethyl 2-amino-6-{[2-oxo-2-(N,N-bis-2-methoxyethyl-amino)-ethoxycarbamoyl]-methyl}-azulene-1,3-dicarboxylate In an analogous manner to that described in Example 1, from diethyl 2-amino-6-[(hydroxycarbamoyl)-methyl]- azulene-1,3-dicarboxylate sodium and N-chloroacetyl-N,N-bis-2-methoxyethyl-amine the title compound of m.p. 109–112° C. is obtained in 31% yield.

EXAMPLE 5

Diethyl 2-amino-6-[(2-oxo-2-N,N-dimethylamino-ethoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and 2-chloro-N,N-dimethylacetamide the title compound of m.p. 177–179° C. is obtained in 27% yield.

EXAMPLE 6

Diethyl 2-amino-6-[(2-oxo-2-ethoxy-ethoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and ethyl bromoacetate the title compound is obtained in 24% yield as a wax.

EXAMPLE 7

Diethyl 2-amino-6-[(2-hydroxy-ethoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and 2-bromoethanol the title compound of m.p. 190–192° C. is obtained in 15% yield.

EXAMPLE 8

Diethyl 2-amino-6-[(2,2-dimethyl-1,3-dioxolan-4-yl-methoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and 2,2-dimethyl-4-(4-methyl-benzenesulphonyloxy-methyl)-1,3-dioxolan the title compound of m.p. 135–137° C. is obtained in 15% yield.

EXAMPLE 9

Diethyl 2-amino-6-[(2,3-dihydroxy-propoxycarbamoyl)-methyl]-azulene-1,3-dicarboxylate By reacting the compound described in Example 8 with dilute hydrochloric acid and subsequent chromatographic purification the title compound of m.p. 151–153° C. is obtained in 13% yield.

EXAMPLE 10

Diethyl 2-amino-6-[(2-hydroxy-3-methoxy-propoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and 2-methoxymethyl-oxirane the title compound is obtained in 15% yield as a wax.

EXAMPLE 11

Diethyl 2-amino-6-{[2-oxo-2-(N,N-bis-2-hydroxyethyl-amino)-ethoxycarbamoyl]-methyl}-azulene-1,3-dicarboxylate In an analogous manner to that described in Example 1, from diethyl 2-amino-6-[(hydroxycarbamoyl)-methyl]-azulene-1,3-dicarboxylate sodium and N-chloroacetyl-N,N-bis-2-hydroxyethyl-amine the title compound is obtained in 23% yield as a wax.

EXAMPLE 12

Diethyl 2-amino-6-{[(N,N-dimethylamino)-carbonyloxy-carbamoyl]-methyl}-azulene-1,3-dicarboxylate In an analogous manner to that described in Example 1, but using N,N-dimethylformamide in place of methanol, from diethyl 2-amino-6-[(hydroxycarbamoyl)-methyl]-azulene-1,3-dicarboxylate sodium and chloroformic acid dimethylamide the title compound of m.p. 167–169° C. is obtained in 17% yield.

EXAMPLE 13

Diethyl 2-amino-6-{[2-oxo-2-(N,N-bis-2-methoxyethyl-amino)-N-methyl-ethoxycarbamoyl]-methyl}-azulene-1,3-dicarboxylate In an analogous manner to that described in Example 1, from diethyl 2-amino-6-[(N-methyl-hydroxycarbamoyl)-methyl]-azulene-1,3-dicarboxylate sodium and N-chloroacetyl-N,N-bis-2-methoxyethyl-amine the title compound is obtained in 60% yield as a wax.

EXAMPLE 14

Diethyl 2-amino-6-[(2-piperidin-1-yl-ethoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and 2-piperidinoethyl bromide the title compound of m.p. 163–165° C. is obtained in 7% yield.

EXAMPLE 15

Diethyl 2-amino-6-[(3-dimethylamino-2-hydroxy-propoxycarbamoyl)-methyl]-azulene-1,3-dicarboxylate A mixture of 1.14 g (3 mmol) of diethyl 2-amino-6-[(hydroxycarbamoyl)-methyl]-azulene-1,3-dicarboxylate sodium, 50 ml of ethanol, 0.1 ml of triethylamine and 0.25 ml of epichlorohydrin is heated to reflux for 20 hours, subsequently concentrated and the residue is chromatographed on silica gel. Elution with isohexane:ethyl acetate 1:1 gives 0.2 g of the desired epoxide which is treated with excess ethanolic dimethylamine solution. After standing at room temperature for one day the mixture is chromatographed on silica gel. Elution with isohexane:ethyl acetate 1:1 gives 60 mg (4% of theory) of the title compound as a wax.

EXAMPLE 16

Diethyl 2-amino-6-[(diethoxy-phosphorylmethoxycarbamoyl)-methyl]-azulene-1,3-dicaboxylate.

A solution of 2.5 mmol of diethyl 2-amino-6-carboxymethyl-azulene-1,3-dicarboxylate in 50 ml of tetrahydrofuran is treated portionwise at 45° C. with 2.5 mmol of N,N-carbonyldiimidazole. The mixture is stirred for 30 minutes, a solution of 2.5 mmol of diethoxyphosphoryl-methoxylamine (L. Maier, Phosphorus, Sulphur, and Silicon 1993, Vol. 76, 119–122) in 20 ml of tetrahydrofuran is added and the resulting mixture is heated to reflux for 3 hours. The mixture is concentrated and the residue is chromatographed on silica gel. Elution with isohexane:ethyl acetate 1:1 gives 78% of the title compound of m.p. 146–147° C.

EXAMPLE 17

Diethyl 2-amino-6-(phosphonomethoxycarbamoyl-methyl)-azulene-1,3-dicarboxylate

In an analogous manner to that described in Example 26, from diethyl 2-amino-6-carboxymethyl-azulene-1,3-dicarboxylate and phosphonomethoxyamine (L. Maier, Phosphorus, Sulfur, and Silicon 1993, Vol. 76, 119–122) the title compound is obtained as an amorphous powder.

EXAMPLE 18

Diethyl 2-amino-6-[(2-oxo-2-pyrrolidin-1-yl-N-methyl-ethoxycarbamoyl)-methyl]-azulene-1,3-dicarboxylate In an analogous manner to that described in Example 1, from diethyl 2-amino-6-[(N-methyl-hydroxycarbamoyl)-methyl]-azulene-1,3-dicarboxylate sodium and N-chloroacetyl-pyrrolidine the title compound is obtained in 77% yield as a wax.

EXAMPLE 19

Diethyl 2-amino-6-[(2-amino-2-oxo-ethoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and 2-chloroacetamide the title compound of m.p. 208–210° C. is obtained in 26% yield.

EXAMPLE 20

Diethyl 2-amino-6-{([2-(morpholin-1-yl)-ethoxycarbamoyl]-methyl}-azulene-1,3-dicarboxylate In an analogous manner to that described in Example 1, from diethyl 2-amino-6-[(hydroxycarbamoyl)-methyl]-azulene-1,3-dicarboxylate sodium and 2-morpholinoethyl chloride the title compound of m.p. 198–200° C. is obtained in 37% yield.

EXAMPLE 21

Diethyl 2-amino-6-{[3-(N,N-bis-2-methoxyethyl-amino)-propoxycarbamoyl]-methyl}-azulene-1,3-dicarboxylate In an analogous manner to that described in Example 1, from diethyl 2-amino-6-[(hydroxycarbamoyl)-methyl]-azulene-1,3-dicarboxylate sodium and 3-(N,N-bis-2-methoxyethyl-amino)-propyl chloride the title compound of m.p. 113–115° C. is obtained in 49% yield.

EXAMPLE 22

Diethyl 2-amino-6-{[(3-oxo-3-ethoxy)-2-propoxycarbamoyl]-methyl}-azulene-1,3-dicarboxylate In an analogous manner to that described in Example 1, from diethyl 2-amino-6-[(hydroxycarbamoyl)-methyl]-azulene-1,3-dicarboxylate sodium and ethyl 2-bromopropionate the title compound of m.p. 173–175° C. is obtained in 40% yield.

EXAMPLE 23

Diethyl 2-amino-6-{[(3-(piperidin-1-yl)-propoxycarbamoyl]-methyl}-azulene-1,3-dicarboxylate In an analogous manner to that described in Example 1, from diethyl 2-amino-6-[(hydroxycarbamoyl)-methyl]-azulene-1,3-dicarboxylate sodium and 3-piperidinopropyl chloride the title compound of m.p. 174–176° C. is obtained in 43% yield.

EXAMPLE 24

Diethyl 2-amino-6-[(3-diethylamino-propoxycarbamoyl)-methyl]-azulene-1,3-dicarboxylate In an analogous manner to that described in Example 1, from diethyl 2-amino-6-[(hydroxycarbamoyl)-methyl]-azulene-1,3-dicarboxylate sodium and 3-diethylamino-propyl chloride the title compound of m.p. 125–127° C. is obtained in 42% yield.

EXAMPLE 25

Diethyl 2-amino-6-{[(3-amino-3-oxo)-2-propoxycarbamoyl]-methyl}-azulene-1,3-dicarboxylate In an analogous manner to that described in Example 1, from diethyl 2-amino-6-[(hydroxycarbamoyl)-methyl]-azulene-1,3-dicarboxylate sodium and 2-chloropropionamide the title compound of m.p. 232–234° C. is obtained in 19% yield.

EXAMPLE 26

Diethyl 2-amino-6-{([(2-methylamino-2-oxo)-ethoxycarbamoyl]-methyl}-azulene-1,3-dicarboxylate In an analogous manner to that described in Example 1, from diethyl 2-amino-6-[(hydroxycarbamoyl)-methyl]-azulene-1,3-dicarboxylate sodium and chloroacetic acid N-methylamide the title compound of m.p. 194–196° C. is obtained in 24% yield.

EXAMPLE 27

Diethyl 2-amino-6-{[(2-ethylamino-2-oxo)-ethoxycarbamoyl]-methyl}-azulene-1,3-dicarboxylate In an analogous manner to that described in Example 1, from diethyl 2-amino-6-[(hydroxycarbamoyl)-methyl]-azulene-1,3-dicarboxylate sodium and chloroacetic acid N-ethylamide the title compound of m.p. 176–178° C. is obtained in 21% yield.

EXAMPLE 28

Diethyl 2-amino-6-{[(2-n-butylamino-2-oxo)-ethoxycarbamoyl]-methyl}-azulene-1,3-dicarboxylate In an analogous manner to that described in Example 1, from diethyl 2-amino-6-[(hydroxycarbamoyl)-methyl]- azulene-1,3-dicarboxylate sodium and chloroacetic acid N-n-butylamide the title compound of m.p. 148–1500° C. is obtained in 33% yield.

EXAMPLE 29

Diethyl 2-amino-6-{[(N-methylamino)-carbonyloxy-carbamoyl]-methyl}-azulene-1,3-dicarboxylate A mixture of 0.2 g (0.55 mmol) of diethyl 2-amino-6-[(hydroxycarbamoyl)-methyl]-azulene-1,3-dicarboxylate, 5 ml of dimethyl sulphoxide and 35 □l (0.6 mmol) of methyl isocyanate is stirred at room temperature for 18 hours. Thereafter, the mixture is diluted with water, extracted with dichloromethane and the extract is chromatographed on silica gel. Elution with ethyl acetate gives 60 mg (36% of theory) of the title compound of m.p. 222–224° C.

EXAMPLE 30

Diethyl 2-amino-6-{[(N-n-butylamino)-carbonyloxy-carbamoyl]-methyl}-azulene-1,3-dicarboxylate In an analogous manner to that described in Example 29, from diethyl 2-amino-6-[(hydroxycarbamoyl)-methyl]-azulene-1,3-dicarboxylate und n-butyl isocyanate the title compound of m.p. 178–179° C. is obtained in 47% yield.

EXAMPLE 31

Diethyl 2-amino-6-{[(4-methyl-piperazino)-carbonyloxy-carbamoyl]-methyl}-azulene-1,3-dicarboxylate 90 mg of N,N'-carbonyldiimidazole are added to a mixture of 0.2 g (0.55 mmol) of diethyl 2-amino-6-[(hydroxycarbamoyl)-methyl]-azulen-1,3-dicarboxylate and 20 ml of dichloromethane, the resulting mixture is stirred at room temperature for 2 hours, 61 □l (0.55 mmol) of N-methyl-piperazine are added dropwise thereto and the mixture obtained is stirred for 1 hour. The mixture is concentrated and the residue is triturated with ethyl acetate, there being isolated 152 mg (57% of theory) of the title compound as a wax.

EXAMPLE 32

Diethyl 2-amino-6-{[(1-morpholino)-carbonyloxy-carbamoyl)-methyl}-azulene-1,3-dicarboxylate In an analogous manner to that described in Example 31, from diethyl 2-amino-6-[(hydroxycarbamoyl)-methyl]-azulene-1,3-dicarboxylate und morpholine the title compound is obtained in 61% yield as a wax.

EXAMPLE 33

Diethyl 2-amino-6-{[(4-amino-butylamino)-carbonyloxy-carbamoyl]-methyl}-azulene-1,3-dicarboxylate 45 mg of N,N'-carbonyldiimidazole are added to a mixture of 0.1 g (0.28 mmol) of diethyl 2-amino-6-[(hydroxycarbamoyl)-methyl]-azulene-1,3-dicarboxylate and 10 ml of dichloromethane, the resulting mixture is stirred at room temperature for 2 hours, treated with 36 mg of N-methyldiisopropylamine and 107 mg (0.28 mmol) of 4-(N-tritylamino)-butylamine and stirred for 1 hour. The mixture is concentrated and the residue is chromatographed on silica gel. Elution with methyl acetate: heptane 3:1 gives 100 mg of trityl compound which is dissolved in 3 ml of dichloro- methane and treated with 500 □l of trifluoroacetic acid. After stirring for 10 minutes the mixture is concentrated and the residue is triturated with diethyl-ether. 68 mg (51% of theory) of the title compound of m.p. 150–150° C. are isolated.

EXAMPLE 34

Diethyl 2-amino-6-[(ethoxycarbonyloxy-carbamoyl)-methyl]-azulene-1,3-dicarboxylate In an analogous manner to that described in Example 12, from diethyl 2-amino-6-[(hydroxycarbamoyl)-methyl]-azulene-1,3-dicarboxylate and ethyl chloroformate the title compound is obtained in 47% yield as an oil.

What is claimed is:

1. Compounds of the formula

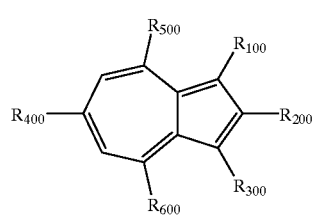

Ia wherein $R_{100}$ and $R_{300}$ each independently signify hydrogen or $C_1$–$C_6$-alkoxycarbonyl, $R_{200}$ signifies hydrogen, amino, $C_1$–$C_6$-alkylcarbonylamino or di-$C_1$–$C_6$-alkylcarbonylamino, $R_{400}$ signifies $R_{800}XON(R_7)COCH_2$—, $R_{500}$ and $R_{600}$ each independently signify hydrogen or $C_1$–$C_6$-alkoxy, $R_7$ signifies hydrogen or $C_1$–$C_6$-alkyl, X signifies a valency bond, $C_1$–$C_6$-alkylene, carbonyl or $C_1$–$C_6$-carbonylalkylene, $R_{800}$ signifies $C_1$–$C_6$, which may be substituted by one or more same or different substituents selected from hydroxy, amino, $C_1$–$C_6$-alkylamino and di-$C_1$–$C_6$-alkylamino, 2,2-di-$C_1$–$C_6$-alkyl-1,3-dioxolan-4-yl or $PO(OR_{13})(OR_4)$, and, when X signifies other than a valency bond, $R_{800}$ also signifies hydroxy, $C_1$–$C_6$-alkoxy, hydroxy-$C_1$–$C_6$-alkyl or $NR_{900}R_{1000}$, $R_{900}$ and $R_{1000}$ each individually signify hydrogen, $C_1$–$C_6$-alkyl, which may carry one or more same or different substituents selected from hydroxy, $C_1$–$C_6$-alkoxy and amino and $R_{13}$ and $R_{14}$ each individually signify hydrogen or $C_1$–$C_6$-alkyl, as well as their tautomers, enantiomers, diastereomers, racemates and physiologically compatible salts or esters.

2. Compounds according to claim 1 of the formula

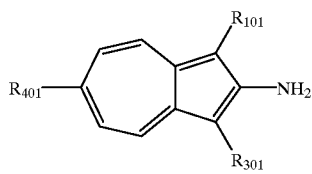

Ib wherein $R_{101}$ and $R_{301}$ signify $C_1$–$C_6$-alkoxycarbonyl, $R_{401}$ signifies $R_{801}XON(R_7)COCH_2$—, $R_7$ signifies hydrogen or $C_1$–$C_6$-alkyl, X signifies a valency bond, $C_1$–$C_6$-alkylene, carbonyl or $C_1$–$C_6$-carbonylalkylene, $R_{801}$ signifies $C_1$–$C_6$, which may be substituted by one or more same or different substituents selected from hydroxy, amino, $C_1$–$C_6$-alkylamino and di-$C_1$–$C_6$-alkylamino, 2,2-di-$C_{1-C6}$-alkyl-1,3-dioxolan-4-yl or $PO(OR_{13})(OR_4)$, and, when X signifies other than a valency bond, $R_{801}$ also signifies hydroxy, $C_1$–$C_6$-alkoxy or $NR_{901}R_{1001}$, $R_{901}$ and $R_{1001}$ each individually signify hydrogen, $C_1$–$C_6$-alkyl, which may carry one or more same or different substituents selected from hydroxy, $C_1$–$C_6$-alkoxy and amino and $R_{13}$ and $R_{14}$ each individually signify hydrogen or $C_1$–$C_6$-alkyl, as well as their tautomers, enantiomers, diastereomers, racemates and physiologically compatible salts or esters.

3. Compounds according to claim 2 of the formula

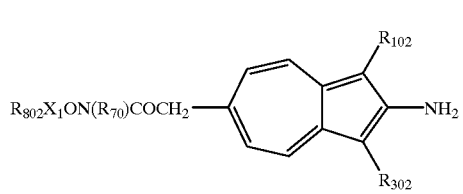

Ic wherein $R_{102}$ and $R_{302}$
signify methoxycarbonyl, ethoxycarbonyl or tbutoxycarbonyl, $R_{70}$
signifies hydrogen or methyl, $X_1$ signifies carbonylmethylene, ethylene or a valency bond, $R_{802}$
signifies 2,3-dihydroxypropyl, 2-hydroxy-3-methoxypropyl, 2,2-dimethyl-1,3-dioxolan-4-yl, 3-dimethylamino-2-hydroxypropyl or, where $X_1$ signifies other than a valency bond, also hydroxy, ethoxy or —$NR_{902}R_{1002}$, $R_{902}$ and $R_{1002}$
each individually signify methoxyethyl, methyl or hydroxyethyl, as well as their tautomers, enantiomers, diastereomers, racemates and physiologically compatible salts or esters.

4. The compound according to claim 3, diethyl 2-amino-6-{[2-oxo-2-(N,N-bis-2-methoxyethyl-amino)-ethoxycarbamoyl]-methyl}-azulene-1,3-dicarboxylate.

5. A pharmaceutical preparation containing a compound of claim 1 and a therapeutically inert carrier for the treatment and prophylaxis of inflammatory diseases.

6. A method for treatment of inflammatory disease which comprises administering to an affected patient a compound of claim 1 and a pharmaceutically acceptable carrier in an amount effective for treatment of the inflammatory disease.

7. A compound of claim 3 wherein $R_{102}$ and $R_{302}$ are ethoxycarbonyl.

8. A compound of claim 1 which is diethyl 2-amino-6-[(2-oxo-2-N,N-dimethylamino-ethoxycarbamoyl)-methyl]-azulene-1,3-dicarboxylate.

9. A compound of claim 1 which is diethyl 2-amino-6-[(2-oxo-2-ethoxy-ethoxycarbamoyl)-methyl]-azulene-1,3-dicarboxylate.

10. A compound of claim 1 which is diethyl 2-amino-6-[(2-hydroxy-ethoxycarbamoyl)-methyl]-azulene-1,3-dicarboxylate.

11. A compound of claim 1 which is diethyl 2-amino-6-[(2,3-dihydroxy-propoxycarbamoyl)-methyl]-azulene-1,3-dicarboxylate.

12. A compound of claim 1 which is diethyl 2-amino-6-[(2-hydroxy-3-methoxy-propoxycarbamoyl)-methyl]-azulene-1,3-dicarboxylate.

13. A compound of claim 1 which is diethyl 2-amino-6-{[2-oxo-2-(N,N-bis-2-hydroxyethyl-amino)-ethoxycarbamoyl]-methyl}-azulene-1,3-dicarboxylate.

14. A compound of claim 1 which is diethyl 2-amino-6-{[(N,N-dimethylamino)-carbonyloxy-carbamoyl]-methyl}-azulene-1,3-dicarboxylate.

15. diethyl 2-amino-6-{[2-oxo-2-(N,N-bis-2-methoxyethyl-amino)-N-methyl-ethoxycarbamoyl]-methyl}-azulene-1,3-dicarboxylate.

16. A compound of claim 1 which is diethyl 2-amino-6-[(3-dimethylamino-2-hydroxy-propoxycarbamoyl)-methyl]-azulene-1,3-dicarboxylate.

17. A compound of claim 1 which is diethyl 2-amino-6-[(diethoxy-phosphorylmethoxycarbamoyl)-methyl]-azulene-1,3-dicarboxylate.

18. A compound of claim 1 which is diethyl 2-amino-6-(phosphonomethoxycarbamoyl-methyl)-azulene-1,3-dicarboxylate.

19. A compound of claim 1 which is diethyl 2-amino-6-[(2-amino-2-oxo-ethoxycarbamoyl)-methyl]-azulene-1,3-dicarboxylate.

20. A compound of claim 1 which is diethyl 2-amino-6-{[3-(N,N-bis-2-methoxyethyl-amino)-propoxycarbamoyl]-methyl}-azulene-1,3-dicarboxylate.

21. A compound of claim 1 which is diethyl 2-amino-6-[(3-oxo-3-ethoxy-2-propoxycarbamoyl)]-methyl]-azulene-1,3-dicarboxylate.

22. A compound of claim 1 which is diethyl 2-amino-6-[(3-diethylamino-propoxycarbamoyl)-methyl]-azulene-1,3-dicarboxylate-diethylester.

23. A compound of claim 1 which is diethyl 2-amino-6-[(3-oxo-3-ethoxy-2-propoxycarbamoyl)-methyl]-azulene-1,3-dicarboxylate.

24. A compound of claim 1 which is diethyl 2-amino-6-{[(2-methylamino-2-oxo)-ethoxycarbamoyl]-methyl}-azulene-1,3-dicarboxylate.

25. A compound of claim 1 which is diethyl 2-amino-6-{[(2-ethylamino-2-oxo)-ethoxycarbamoyl]-methyl}-azulene-1,3-dicarboxylate.

26. A compound of claim 1 which is diethyl 2-amino-6-{[(2-n-butylamino-2-oxo)-ethoxycarbamoyl]-methyl}-azulene-1,3-dicarboxylate.

27. A compound of claim 1 which is diethyl 2-amino-6-{[(N-methylamino)-carbonyloxy-carbamoyl]-methyl}-azulene-1,3-dicarboxylate.

28. A compound of claim 1 which is diethyl 2-amino-6-{[(N-n-butylamino)-carbonyloxy-carbamoyl]-methyl}-azulene-1,3-dicarboxylate.

29. A compound of claim 1 which is diethyl 2-amino-6-{[(4-amino-butylamino)-carbonyloxy-carbamoyl]-methyl}-azulene-1,3-dicarboxylate.

30. A compound of claim 1 which is diethyl 2-amino-6-[(ethoxycarbonyloxy-carbamoyl)-methyl]-azulene-1,3-dicarboxylate.

* * * * *